US012740990B2

(12) United States Patent
Park et al.

(10) Patent No.: US 12,740,990 B2
(45) Date of Patent: Sep. 22, 2026

(54) COMPOSITION CONTAINING HOMOHARRINGTONINE AS ACTIVE INGREDIENT FOR PREVENTING OR TREATING MUSCLE DISEASES

(71) Applicant: RESEARCH COOPERATION FOUNDATION OF YEUNGNAM UNIVERSITY, Gyeongsan-si (KR)

(72) Inventors: So-Young Park, Daegu (KR); Hanbyul Jung, Daegu (KR); Hye-Na Cha, Daegu (KR); Soyoung Park, Daegu (KR); Jae-Ryong Kim, Daegu (KR); Eok-Cheon Kim, Wonju-si (KR)

(73) Assignee: RESEARCH COOPERATION FOUNDATION OF YEUNGNAM UNIVERSITY, Gyeongsan-si (KR)

( * ) Notice: Subject to any disclaimer, the term of this patent is extended or adjusted under 35 U.S.C. 154(b) by 372 days.

(21) Appl. No.: 18/563,916

(22) PCT Filed: Jan. 18, 2022

(86) PCT No.: PCT/KR2022/000910
§ 371 (c)(1),
(2) Date: Nov. 24, 2023

(87) PCT Pub. No.: WO2022/255583
PCT Pub. Date: Dec. 8, 2022

(65) Prior Publication Data

US 2024/0252510 A1 Aug. 1, 2024

(30) Foreign Application Priority Data

May 31, 2021 (KR) ........................ 10-2021-0069690

(51) Int. Cl.
*A61K 31/55* (2006.01)
*A61P 21/00* (2006.01)

(52) U.S. Cl.
CPC .............. *A61K 31/55* (2013.01); *A61P 21/00* (2018.01)

(58) Field of Classification Search
CPC ................................ A61K 31/55; A61P 21/00
See application file for complete search history.

(56) References Cited

U.S. PATENT DOCUMENTS 4,675,318 A * 6/1987 Liu ........................ A61K 36/23
514/215
2022/0023309 A1* 1/2022 Kim ....................... A61K 31/55

FOREIGN PATENT DOCUMENTS

CN 106608879 A 5/2017
KR 10-1825637 B1 2/2018
(Continued)

OTHER PUBLICATIONS

WO-2019078381-A1—machine translation—Google Patents—printed Feb. 21, 2026. (Year: 2026).*
(Continued)

*Primary Examiner* — George W Kosturko
*Assistant Examiner* — Izabela Schmidt
(74) *Attorney, Agent, or Firm* — Revolution IP, PLLC

(57) ABSTRACT

The present invention relates to a composition for preventing or treating muscle diseases, wherein the composition contains homoharringtonine as an active ingredient, wherein it was found that the suppression of a decrease in skeletal muscle mass and improved muscle strength were exhibited in an experimental group in which homoharringtonine was administered to an animal model in which reduction in muscle mass and muscular atrophy were induced by obesity, aging, or the fixing of lower extremities, and thus the composition including homoharringtonine as an active ingredient can be provided as a pharmaceutical composition
(Continued)

or a health food for preventing or treating muscle diseases caused by a decrease in muscle mass or muscle strength.

6 Claims, 5 Drawing Sheets

(56) References Cited

FOREIGN PATENT DOCUMENTS

| | | | | |
|---|---|---|---|---|
| KR | 10-2018-0048416 A | | 5/2018 | |
| KR | 10-2018-0085124 A | | 7/2018 | |
| KR | 10-2019-0099613 A | | 8/2019 | |
| KR | 10-2020-0072924 A | | 6/2020 | |
| KR | 10-2209386 B1 | | 2/2021 | |
| WO | WO-2019078381 A1 | * | 4/2019 | A61K 47/10 |
| WO | WO-2020122391 A1 | * | 6/2020 | A61K 31/55 |

OTHER PUBLICATIONS

Oxford English Dictionary, https://www.oed.com/dictionary/prevent_v?tab=meaning_and_use#28270689, printed Feb. 17, 2026. (Year: 2026).*
Chen et al., Proc Natl Acad Sci U S A. Feb. 5, 2019;116(6):2220-2225. (Year: 2019).*
Li et al., J Mol Med (Berl). Oct. 2008; 86(10): 1113-1126. (Year: 2008).*
Kantarjian et al., Clin Lymphoma Myeloma Leukemia. (2013) 13:530-3. (Year: 2013).*
Dorst et al., Ther Adv Neurol Disord 2018, vol. 11: 1-16. (Year: 2018).*
NIH: Inflammatory Myopathies National Institute of Neurological Disorders and Stroke, printed Feb. 14, 2026. (Year: 2026).*
Amyotrophic Lateral Sclerosis (ALS) | National Institute of Neurological Disorders and Stroke, printed Feb. 14, 2026. (Year: 2026).*
Chen (Chen et al., Proc Natl Acad Sci U S A. Feb. 5, 2019;116(6):2220-2225)—Supplementary Information. (Year: 2019).*
Kim et al., Front. Pharmacol. 11:1032. doi: 10.3389/fphar.2020.01032. (Year: 2020).*
Lü S, Wang J. J Hematol Oncol. Jan. 3, 2014;7:2. (Year: 2014).*
International Search Report of PCT/KR2022/000910 mailed Aug. 31, 2022 from Korean Intellectual Property Office.
Annabelle Z. Caron et al., "A novel hindlimb immobilization procedure for studying skeletal muscle atrophy and recovery in mouse", Journal of Applied Physiology, Jun. 1, 2009, vol. 106, No. 6, pp. 2049-2059.
Francis Robert et al., "Targeting Protein Synthesis in a Myc/mTOR-Driven Model of Anorexia-Cachexia Syndrome Delays Its Onset and Prolongs Survival", Cancer Research, Dec. 2011, vol. 72, No. 3, pp. 747-756.
Maryam Pouryahya et al., "Characterizing Cancer Drug Response and Biological Correlates A Geometric Network Approach", Scientific Reports, 2015, vol. 8, Article No. 6402.

* cited by examiner

COMPOSITION CONTAINING HOMOHARRINGTONINE AS ACTIVE INGREDIENT FOR PREVENTING OR TREATING MUSCLE DISEASES

CROSS REFERENCE TO PRIOR APPLICATIONS

This application is a National Stage Application of PCT International Patent Application No. PCT/KR2022/000910 filed on Jan. 18, 2022, under 35 U.S.C. § 371, which claims priority to Korean Patent Application No. 10-2021-0069690 filed May 31, 2021, respectively, which are all hereby incorporated by reference in their entirety.

TECHNICAL FIELD

The present disclosure relates to a composition for preventing or treating muscle diseases including homoharringtonine as an active ingredient.

BACKGROUND ART

The number of elderly people continues to grow worldwide, and it is predicted that the number of people aged 65 or older will reach 25% in Europe and North America and 2 billion worldwide by 2050. According to EWGSOP, 5-13% of people aged 60-70 have sarcopenia, and 50% of people over 80 are affected by sarcopenia. Korea is the fastest-aging country in the world, and according to the 2019 resident registration statistics, the number of people over 65 exceeded 8 million. The prevalence of sarcopenia between the age of 70 to 84 in Korea was 21.3% for men and 13.8% for women (Korean Frailty and Aging Cohort Study), and the number of patients affected by sarcopenia is expected to grow as the elderly population in Korea increases.

It is proposed that the aging of skeletal muscles is a major cause of physical disorders such as fractures and falls, as well as metabolic diseases including diabetes, and is known to be an important cause that deteriorates the quality of life in the elderly. Recently, it has been reported that the aging of skeletal muscle is related to the aging of other tissues and the life of the living body, and this is because skeletal muscle-derived myokine or miRNA affects not only the skeletal muscle but also the function of other tissues through the blood.

In the United States, sarcopenia was given a diagnostic code in 2016, and soon afterward, the World Health Organization included it in the 11*th* International Classification of Diseases. Though sarcopenia is to be included as a diagnostic code in the 8*th* revision of the Korean Standard Classification of Disease and Cause of Death in Korea in 2021 and thus many pharmaceutical companies are currently developing and conducting clinical trials on drugs to control aging by targeting myokine, there is no treatment yet, with the recognition that diet and exercise are the best treatment yet so far.

DISCLOSURE OF THE INVENTION

Technical Goals

An object of the present disclosure is to provide a composition including homoharringtonine as an active ingredient to provide as a pharmaceutical composition and health food for preventing or treating sarcopenia by inhibiting skeletal muscle volume and muscle strength.

Technical Solutions

The present disclosure provides a pharmaceutical composition for preventing or treating muscle diseases including homoharringtonine as an active ingredient.

In addition, the present disclosure provides a health food for preventing or ameliorating muscle diseases including homoharringtonine as an active ingredient.

Advantageous Effects

According to the present disclosure, it was found in the experiments, in which homoharringtonine administration to animals with muscle loss and muscular atrophy by obesity, aging, or lower limb fixation attenuates the reduction in skeletal muscle mass and improves muscle strength, such that a composition including the homoharringtonine as an active ingredient may be provided as a pharmaceutical composition and health food for preventing or treating muscle diseases due to reduction in muscle mass or muscle strength.

BRIEF DESCRIPTION OF DRAWINGS

FIGS. 1A-1C are the results of body weight, amount of dietary intake, and weight of gastrocnemius in high-fat diet-induced obese animals, wherein FIG. 1A shows the result of a change in body weight over time in a normal diet group (Ch), a high-fat diet-fed phosphate-buffer saline-administered group (HF-PBS; high-fat diet fed control group), and a high-fat diet with homoharringtonine-administered group (HF-HHT; high-fat diet fed drug group), and FIGS. 1B and 1C are the results of a cumulative amount of dietary intake and weight of gastrocnemius, respectively, wherein the weight of gastrocnemius was corrected by body weight (expressed in % of body weight). There was a significant increase in the body weight in the mice fed with a high-fat diet, compared to the mice fed with a normal diet. In the high-fat diet group, the body weight was significantly reduced in the homoharringtonine-administered group compared to the phosphate-buffered saline-administered group. However, there was no significant difference in the cumulative amount of dietary intake. The weight of gastrocnemius was significantly lower in the high-fat diet-fed group than in the normal diet-fed group. However, it was significantly higher in the high-fat diet with homoharringtonine group than in the high-fat diet with the phosphate-buffered saline group.

FIGS. 2A-2F are the results of body weight, amount of dietary intake, muscle strength, and muscle weight of old mice, wherein FIG. 2A is the result of a change in body weight during the administration of homoharringtonine in 18-month-old mice, FIG. 2B is a graph showing a cumulative amount of dietary intake, FIG. 2C is the result of muscle strength through an inverted cling test after administering homoharringtonine for 14 weeks, FIG. 2D is the result of gastrocnemius weight after sacrificing the mice, FIG. 2E is the result of body weight 6 months after the administration of homoharringtonine, and FIG. 2F is the result of grip strength 6 months after administration of homoharringtonine. In old mice, the administration of homoharringtonine did not show a significant difference in the body weight and cumulative amount of dietary intake compared to the administration of phosphate-buffered saline. The duration time for inverted clinging was significantly higher in the homoharringtonine-administered group, and the gastrocnemius weight was also significantly higher in the homoharringtonine-administered group. As the result of the 6 months administration of homoharringtonine, there was no significant difference in body weight, but grip strength was significantly higher in the experimental group administered with homoharringtonine.

FIGS. 3A-3D are the results of body weight, amount of dietary intake, and weight of gastrocnemius and tibialis muscle in an animal model with lower limb fixation-induced muscular atrophy, wherein FIG. 3A is the result of a change in body weight in the animal model with lower limb fixation-induced muscular atrophy, FIG. 3B is the graph showing the cumulative amount of dietary intake, FIG. 3C is the result of a change in gastrocnemius weight, and FIG. 3D is the result of a change in tibialis muscle weight. There was no difference in the body weight and cumulative amount of dietary intake between a control group administered with phosphate-buffered saline and an experimental group administered with homoharringtonine For gastrocnemius, the weight of the fixed left leg was significantly lower than that of unfixed the right leg in the control group, whereas there was no significant reduction in muscle weight by fixation in the experimental group administered with homoharringtonine. The tibialis muscle also showed a reduction in weight by fixation in the phosphate-buffered saline-administered group, but there was no difference in the homoharringtonine-administered group.

BEST MODE FOR CARRYING OUT THE INVENTION

Figure 1A:
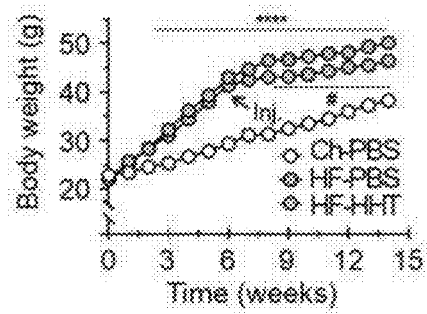
Figure 1B:
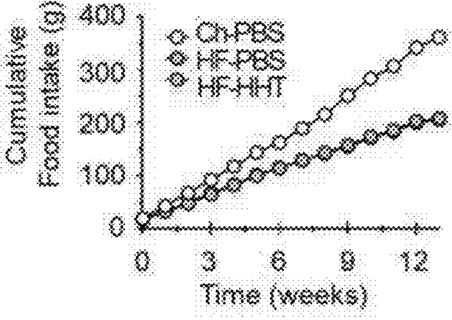
Figure 1C:
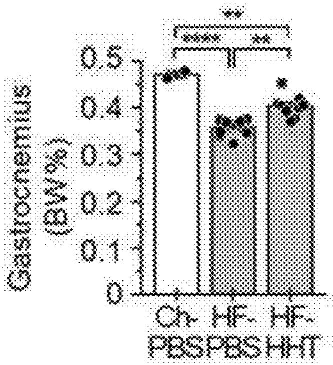

Hereinafter, the present disclosure will be described in more detail.

This patent is supported by the Medical Research Center Program (2022R1A5A2018865) through the National Research Foundation of Korea (NRF) funded by the Korean Ministry of Science and ICT.

Homoharringtonine is a natural mono-component isolated from *Cephalotaxus hainanensis*, used as a therapeutic agent for chronic myeloid leukemia and known to suppress protein production by binding to 80S ribosomes in eukaryotic cells to inhibit chain elongation, but its effect on sarcopenia has not yet been reported. The inventors completed the present disclosure as they found an effect in which homoharringtonine increases skeletal muscle volume and muscle strength in obese and old mice and animal models with lower limb fixation-induced muscular atrophy.

The present disclosure may provide a pharmaceutical composition for preventing or treating muscle diseases including homoharringtonine as an active ingredient.

The muscle disease may be one or more selected from the group consisting of sarcopenia, muscular atrophy, myasthenia, muscular dystrophy, myotonia, hypotonia, muscular weakness, muscular dystrophy, amyotrophic lateral sclerosis, and inflammatory myopathy.

The pharmaceutical composition may include 0.01 to 10 parts by weight of homoharringtonine with respect to a total of 100 parts by weight of the pharmaceutical composition.

The homoharringtonine may inhibit muscle loss and increase muscle strength without a change in body weight.

In an example embodiment of the present disclosure, in the pharmaceutical composition for preventing or treating muscle diseases including the homoharringtonine as an active ingredient, any one formulation selected from the group consisting of injections, granules, powder, tablets, pills, capsules, suppositories, gels, suspensions, emulsions, drops, or liquids according to a conventional method may be used.

In another example embodiment of the present disclosure, the pharmaceutical composition may further include one or more additives selected from the group consisting of appropriate carriers, excipients, disintegrants, sweeteners, coating agents, swelling agents, lubricants, flavoring agents, antioxidants, buffers, bacteriostatic agents, diluents, dispersants, surfactants, binders, and lubricants that are commonly used in the preparation of pharmaceutical compositions.

Specifically, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil may be used as carriers, excipients, and diluents, and solid preparations for oral administration may include tablets, pills, powder, granules, and capsules, wherein such solid preparation may be prepared by mixing, in the composition, at least one or more excipients such as starch, calcium carbonate, sucrose or lactose, and gelatin. In addition to simple excipients, lubricants such as magnesium stearate and talc may also be used. Liquid preparations for oral use include suspensions, solutions, emulsions, and syrups, and various excipients such as wetting agents, sweeteners, fragrances, and preservatives may be included in addition to commonly used simple diluents such as water and liquid paraffin. Preparations for parenteral administration include sterile aqueous solutions, non-aqueous solutions, suspensions, emulsions, freeze-dried preparations, and suppositories. Propylene glycol, polyethylene glycol, vegetable oils such as olive oil, and injectable esters such as ethyl oleate may be used as non-aqueous solvents and suspending agents. Witepsol, macrogol, Tween 61, cacao butter, laurin fat, and glycerogelatin may be used as a base of the suppositories.

According to an example embodiment of the present disclosure, the pharmaceutical composition may be administered to a subject in a conventional manner via intravenous, intraarterial, intraperitoneal, intramuscular, intrasternal, transdermal, intranasal, inhalational, topical, rectal, oral, intraocular, or intradermal routes.

The preferred dosage of the homoharringtonine may vary depending on the subject's condition and weight, the type and extent of a disease, the drug form, and the route and duration of administration, and may be appropriately selected by those skilled in the art. According to an example embodiment of the present disclosure, although not limited thereto, the daily dose may be 0.01 to 200 mg/kg, specifically 0.1 to 200 mg/kg, and more specifically 0.1 to 100 mg/kg. Administration may be conducted once a day or in several divided doses, and the scope of the present disclosure is not limited thereby.

In an example embodiment of the present disclosure, the term 'subject' as used herein may refer to a mammal including a human but is not limited to the examples.

The present disclosure may provide a health food for preventing or ameliorating muscle diseases including homoharringtonine as an active ingredient.

The muscle disease may be one or more selected from the group consisting of sarcopenia, muscular atrophy, myasthenia, muscular dystrophy, myotonia, hypotonia, muscular weakness, muscular dystrophy, amyotrophic lateral sclerosis, and inflammatory myopathy.

The health food may be used in combination with other foods or food additives other than the homoharringtonine and used appropriately according to conventional methods. The mixed amount of the active ingredient may be suitably determined depending on the purpose of use thereof, for example, prevention, health, or therapeutic treatment.

The effective dose of compounds included in the health food may be used in accordance with the effective dose of the therapeutic agent, but in the case of long-term intake for health and hygiene or health control, it may be less than or equal to the above range, and it is certain that the active ingredient may be used in an amount beyond the above range since there is no problem in terms of safety.

The type of health food is not particularly limited, and examples may include meat, sausage, bread, chocolate, candy, snacks, confectionery, pizza, ramen, other noodles, gum, dairy products including ice cream, various soups, beverages, tea, drinks, alcoholic beverages, and vitamin complexes.

MODES FOR CARRYING OUT THE INVENTION

Hereinafter, example embodiments will be described in detail to help the understanding of the present disclosure. However, the following example embodiments are merely illustrative of the content of the present disclosure, and the scope of the present disclosure is not limited to the following examples. The examples of the present disclosure are provided to more completely explain the present disclosure to those skilled in the art.

Experimental Example

The following Experimental Examples are intended to provide Experimental Examples commonly applied to each example embodiment according to the present disclosure.

1) Inverted Cling Test

Mice were placed on a cling wire mesh one by one, and the wire mesh was turned over to measure the time from the beginning until all four feet fell. The wire mesh in a size of 43×34 cm was used as a cling board, and the spacing for each wire was 1.2 cm. The height of the wire mesh was kept at 1.2 m from the bottom, and litter was placed on the bottom to minimize the impact after the fall.

2) Grip Strength Test

The grip strength of each mouse was measured using a grip strength meter (Bioseb, Vitrolles, France). In order to detect an appropriate value, the value was set to 0 for each measurement, and the maximum value of grip strength was measured at least three times by placing the mouse to grasp the meter with both front legs while the body is parallel to the ground surface and then pulling out the tail.

<Example 1> Measurement of Biological Changes by Administration of Homoharringtonine in High-Fat Diet-Induced Obese Animals In a high-fat diet-induced obese animal model, 8-week-old C57BL/6 male mice were divided into a normal diet-fed group and a high-fat diet-fed group, wherein the high-fat diet-fed group was fed with a diet containing 60.3% fat in total calories (#TD.06414, R&D systems, Minneapolis, MN, USA), and the normal diet-fed group was fed with a chow diet (Envigo, Indianapolis, IN, USA). The mice were raised in an environment with a room temperature of 22±2° C. and a 12-hour light and dark period controlled until the end of the experiment, and the weight and amounts of dietary intake were manually measured at 1-week intervals.

As shown in FIGS. 1A-1C, 6 weeks after feeding with the high-fat diet, mice were randomly divided into a control group and an experimental group, and phosphate-buffered saline was administered to the control group and homoharringtonine to the experimental group intraperitoneally. 10 mg of homoharringtonine, a product from TOCRIS in the United Kingdom, was dissolved in 10 mM dimethyl sulfoxide, and 0.545 μg/g body weight per mouse was administered intraperitoneally three times a week for 8 weeks. The normal group was also administered the same dose of phosphate-buffered saline intraperitoneally.

After administration of homoharringtonine in the same process as above, the body weight, amount of dietary intake, and the weight of gastrocnemius were checked in high-fat diet-induced obese mice.

As a result, as shown in FIGS. 1A-IC, the body weight increased significantly 3 weeks after the ingestion in the high-fat diet-fed group compared to the normal diet-fed group. Administration of homoharringtonine started 6 weeks after the high-fat diet intake, and the body weight gain was significantly lower 2 weeks after drug injection in the experimental group administered with homoharringtonine than in the control group administered with phosphate-buffered saline, while no significant difference was observed in the amount of high-fat diet intake between the control group and the experimental group.

In addition, it was found that the weight of gastrocnemius in the lower extremities was significantly lower in the high-fat diet-fed group than in the normal diet-fed group. However, it was significantly higher in the homoharringtonine-administered experimental group than in the phosphate-buffered saline-administered group in high-fat diet-fed mice.

<Example 2> Measurement of Biological Changes by Administration of Homoharringtonine in Old Mouse Models An 18-month-old C57BL/6 was purchased, and maintained in the same breeding environment as above the high-fat diet-induced animal model, and fed with a normal chow diet during the experiment.

After adapting the old mice to the breeding environment for 1 week, they were randomly divided into a control group and an experimental group, and phosphate-buffered saline was administered to the control group and homoharringtonine (0.545 μg/g body weight) was administered to the experimental group intraperitoneally three times a week for more than 4 months.

As a result, as shown in FIGS. 2A-2F, the body weight of old mice tended to decrease 7 weeks after administration in the experimental group administered with homoharringtonine, with no statistically significant difference compared to the control group administered with phosphate-buffered saline. There was also no significant difference in the cumulative amount of dietary intake between the two groups.

Figure 2A:
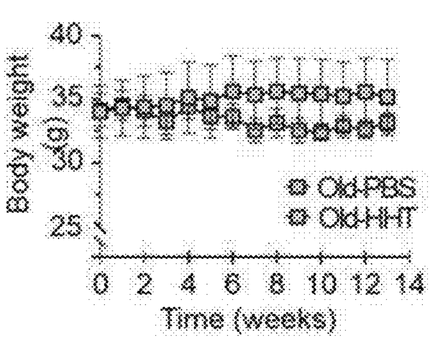
Figure 2B:
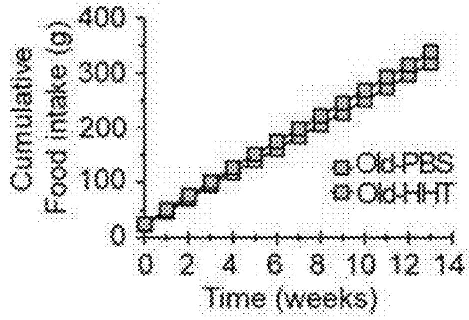
Figure 2C:
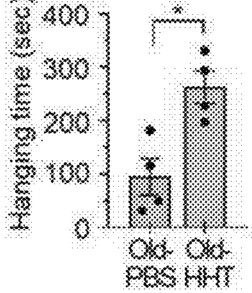
Figure 2D:
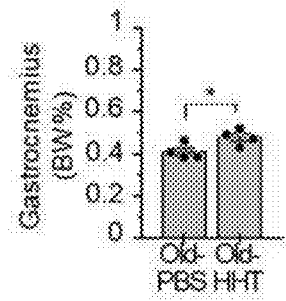
Figure 2E:
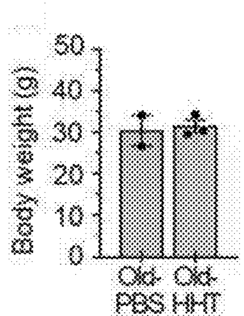
Figure 2F:
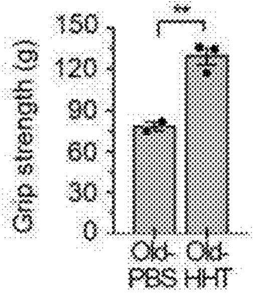

On the other hand, as the result of an inverted cling test to measure the muscle strength of mice, the cling time was significantly higher in the experimental group, as shown in FIG. 2C. In addition, as shown in FIG. 2D, it was found that the weight of gastrocnemius in the lower extremities was significantly higher in the experimental group administered with homoharringtonine than the control group, and in another experimental group as shown in FIG. 2F, after 6 months of homoharringtonine injection, there was no significant difference in the body weight, but the grip strength was significantly enhanced.

<Example 3> Measurement of Biological Changes by Administration of Homoharringtonine in an Animal Model with Lower Limb Fixation-Induced Muscular Atrophy 8-week-old C57BL/6 male mice were adapted to the breeding environment for 1 week and then treated with homoharringtonine for 1 week, and the left lower limb was fixed using a stapler and maintained for 3 weeks. The animal model with lower limb fixation-induced muscular atrophy is an animal model for inducing muscular atrophy by reducing a load of body weight, and induction was conducted using a skin stapler (Manipler AZ, Utsunomiya, Tochigi, Japan) according to a method of Caron et al. (A novel hindlimb immobilization procedure for studying skeletal muscular atrophy and recovery in mouse. J Appl Physiol. 2009 June; 106(6):2049-59.). The unfixed right side was used as a control group.

For a total of 4 weeks from 1 week before fixation to 3 weeks of fixation, phosphate-buffered saline was administered to the control group and homoharringtonine (0.545 μg/g body weight) was administered to the experimental group three times a week intraperitoneally.

Figure 3A:
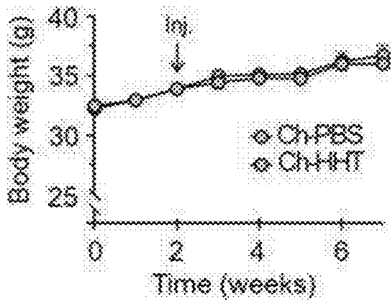
Figure 3B:
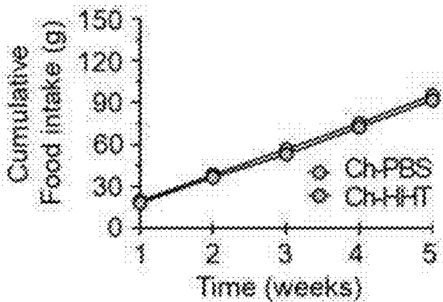

As a result, there was no statistically significant difference in the body weight and amount of dietary intake between the control group and the homoharringtonine administered experimental group, as shown in FIGS. 3A and 3B.

Figure 3C:
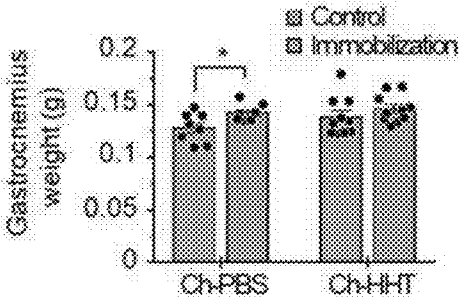
Figure 3D:
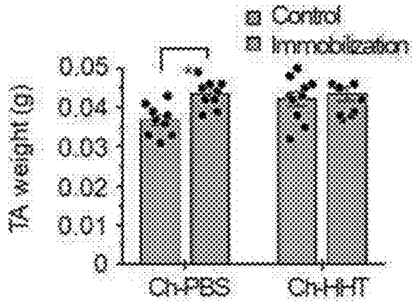

Referring to FIGS. 3C and 3D, the weight of the fixed left skeletal muscle in the control group was significantly lower than the unfixed right side. However, in the drug-injected group, there was no statistically significant difference between the fixed and unfixed legs in both the gastrocnemius and tibialis muscles.

Although specific parts of the present disclosure have been described in detail above, it is clear to those skilled in the art that these specific descriptions are merely preferred example embodiments, and the scope of the present disclosure is not limited thereto. Accordingly, the substantial scope of the present disclosure will be defined by the appended claims and equivalents thereof.

The invention claimed is:

1. A method of treating a muscle disease, comprising:
administering a pharmaceutical composition comprising homoharringtonine as an active ingredient to a subject having the muscle disease,
wherein the muscle disease is sarcopenia or muscular atrophy, and
wherein the homoharringtonine attenuates a reduction in skeletal muscle mass in the subject.

2. The method of claim 1, wherein the sarcopenia or the muscular atrophy is caused by at least one selected from the group consisting of obesity, aging, and lower limb fixation.

3. The method of claim 1, wherein the pharmaceutical composition comprises 0.01 to 10 parts by weight of homoharringtonine with respect to a total of 100 parts by weight of the pharmaceutical composition.

4. The method of claim 1, wherein the homoharringtonine further increases muscle strength without a change in body weight of the subject.

5. A method of ameliorating a muscle disease, comprising:
administering a health food comprising homoharringtonine as an active ingredient to a subject having the muscle disease,
wherein the muscle disease is sarcopenia or muscular atrophy, and
wherein the homoharringtonine attenuates a reduction in skeletal muscle mass in the subject.

6. The method of claim 5, wherein the sarcopenia or the muscular atrophy is caused by at least one selected from the group consisting of obesity, aging, and lower limb fixation.

* * * * *